United States Patent [19]
Baxter et al.

[11] Patent Number: 5,414,284
[45] Date of Patent: May 9, 1995

[54] ESD PROTECTION OF ISFET SENSORS

[76] Inventors: Ronald D. Baxter, Furlong; James G. Connery, Maple Glen; John D. Fogel, Schwenksville; Spencer V. Silverthorne, Perkasie, all of Pa.

[21] Appl. No.: 183,733

[22] Filed: Jan. 19, 1994

[51] Int. Cl.⁶ .................. H01L 29/66; H01L 29/96
[52] U.S. Cl. .................. 257/253; 257/322; 257/355; 257/414
[58] Field of Search .......... 204/406, 416, 418; 257/253, 322, 355, 414

[56] References Cited

U.S. PATENT DOCUMENTS

| | | | |
|---|---|---|---|
| 4,020,830 | 5/1977 | Johnson et al. | 204/418 |
| 4,397,714 | 8/1983 | Janata et al. | 204/406 |
| 4,505,799 | 3/1985 | Baxter | 257/253 |
| 4,589,970 | 5/1986 | Ligtenberg et al. | 204/406 |
| 4,657,658 | 4/1987 | Sibbald | 204/406 |
| 4,851,104 | 7/1989 | Connery et al. | 204/406 |
| 4,961,833 | 10/1990 | Sakai et al. | 204/416 |
| 5,025,298 | 6/1991 | Fey et al. | 257/355 |
| 5,311,042 | 5/1994 | Anceau | 257/355 |

Primary Examiner—Olik Chaudhuri
Assistant Examiner—Brian K. Dutton
Attorney, Agent, or Firm—Joseph J. Kaliko

[57] ABSTRACT

Methods, apparatus and chip fabrication techniques are described which provide electrostatic discharge (ESD) protection to ion-sensitive field effect transistor (ISFET) based devices used to selectively measure ions in a liquid. According to one aspect of the invention, an ESD protection circuit, made up of conventional protective elements, is integrated onto the same silicon chip on which the ISFET is formed, along with an interface that is in contact with the liquid being measured and which does not open up paths for D.C. leakage currents between the ISFET and the liquid. According to a preferred embodiment of the invention, a capacitor structure is used as the interface between the protection circuit and the liquid sample. Further aspects of the invention are directed to methods per se for providing ESD protection for ISFET sensors utilizing the interface means (e.g, capacitor structure) referred to hereinabove, and processes for fabricating the novel interface on a silicon wafer.

13 Claims, 3 Drawing Sheets

ESD PROTECTION OF ISFET SENSORS

BACKGROUND OF THE INVENTION

1. Field of the Invention

The invention relates generally to methods and apparatus for (a) measuring ions in a liquid; (b) protecting such apparatus from the effects of electrostatic discharge; and (c) fabricating such apparatus, including electrostatic discharge protection circuitry, on a silicon wafer.

More particularly, the invention relates to methods, apparatus and chip fabrication techniques which provide electrostatic discharge (ESD) protection to ion-sensitive field effect transistor (ISFET) based devices used to selectively measure ions in a liquid.

According to one aspect of the invention, an ESD protection circuit, made up of conventional protective elements, is integrated onto the same silicon chip on which the ISFET is formed, along with a novel interface. According to the invention, the novel interface is a structure, in contact with the liquid being measured, which does not open up paths for D.C. leakage currents between the ISFET and the liquid.

According to a preferred embodiment of the invention, a capacitor structure is used as the interface between the protection circuit and the liquid sample.

Further aspects of the invention are directed to methods per se for providing ESD protection for ISFET sensors utilizing the interface means (e.g, capacitor structure) referred to hereinabove, and processes for fabricating the novel interface on a silicon wafer.

2. Description of the Related Art

Methods and apparatus for measuring ions in a liquid using an ISFET are well known to those skilled in the art. For example, Johnson, in U.S. Pat. No. 4,020,830, and Connery et al., in U.S. Pat. No. 4,851,104, both incorporated herein by reference to illustrate the state of the art, propose the use of such apparatus. Such devices typically include a measuring circuit and an ISFET immersed in a liquid for selectively measuring ion activity therein.

The aforementioned devices have numerous applications, including applications in the medical and biomedical fields where it is well known to use different ISFETs for measuring different ion activities, such as, for example, pH, pK and pNa.

While semiconductor FET type structures are known to be ESD sensitive, it was, until recently, believed by many that the ISFET structure was largely insensitive to ESD effects because (1) the ISFET does not contain a metallized gate electrode, (which usually is directly involved in electrostatic damage), and (2) experience over time indicated that such devices could be handled by many people without any evidence of electrostatic damage. Testing of ISFET electrodes has, however, indicated that large device shifts can occur following an ESD event.

Those skilled in the art will recognize that although attempts have been made to address the problem of preventing ESD damage in an ISFET based sensors; the known approaches for solving this problem contain inherent limitations, particularly when fabricating the sensor on a silicon wafer.

Before describing these limitations, examples of state of the art apparatus for protecting ISFET based sensors from ESD events will be set forth for comparison with the type of ESD protection methods and apparatus contemplated by the invention.

It will be demonstrated herein that ESD damage can be prevented (in accordance with the teachings of the invention) by using protection circuitry (within an ISFET based probe assembly) that allows build up of charge in a test sample during an ESD event, while simultaneously transferring the charge to the ISFET's source, drain and substrate.

This approach to providing ESD protection minimizes the field developed across the transistor's insulator structure by rapidly equalizing charges on either side of the insulator during an ESD event.

An ESD damage protection circuit for performing the above function could use, for example, fast bi-directional zener diodes connected between the test liquid and the transistor's source, drain and substrate conductors, as will be described in detail hereinafter with reference to the drawing.

The electrical contact to the test liquid can be achieved using a counter electrode, such as the counter electrode is described in the aforementioned U.S. Pat. No. 4,851,104, previously incorporated herein by reference.

Another example of state of the art apparatus for selectively measuring ions in a liquid and protecting against ESD events, is set forth by Ligtenberg et al., in U.S. Pat. No. 4,589,970. The U.S. Pat. No. 4,589,970 patent is incorporated herein by reference for its description of an ESD protection circuit used in an ISFET based sensor.

The ESD protection circuit taught in the incorporated U.S. Pat. No. 4,589,970 patent comprises at least one electrode, connected via a low impedance contact to the liquid being sampled, coupled to the ISFET by a protective element having a low impedance for high voltages and a high resistance to low voltages.

The incorporated U.S. Pat. No. 4,589,970 patent states that unidirectional zener diodes, capacitors, mechanical switches and high threshold voltage MOSFETS can be used in place of or in parallel with the bi-directional zeners to protect against ESD events.

The use of discrete components mounted in the probe package to form the protection circuit and/or the integration of the circuit onto the ISFET's silicon substrate is proposed by the incorporated U.S. Pat. No. 4,589,970 patent.

As for the limitations referred to hereinbefore, one road block to the integration of the protection circuit described in the incorporated U.S. Pat. No. 4,589,970 patent (and any similar circuitry) onto the ISFET's silicon substrate is the difficulty in creating a metal electrode that provides a reliable low-impedance contact to the liquid.

The incorporated U.S. Pat. No. 4,589,970 patent suggests the use of aluminum or polysilicon films to form the contact; however, both films are subject to chemical attack in many of the liquids that would be measured by the ISFET.

An alternative would be to deposit a film comprised of a noble metal such as gold or platinum for the contact. Unfortunately gold and platinum films usually require an intermediate layer using materials such as titanium or chromium to provide good adhesion to the substrate; thus, the chemical resistance of the electrode could be compromised by the addition of another film especially if pinholes occur in the noble metal film.

Another concern that exists when a low impedance metal contact is used between the test liquid (sample) and the protection circuit is that paths are opened up for D.C. leakage currents via the protection circuit between the sample and the ISFET source, drain and substrate.

Accordingly, it would be desirable if methods and apparatus were available which provide ESD protection to ISFET based devices used to selectively measure ions in a liquid, using (a) an ESD protection circuit made up of conventional protective elements integrated onto the same silicon chip on which the ISFET is formed; and (b) an interface means, in contact with the liquid being measured, which does not open up paths for D.C. leakage currents between the ISFET and the liquid.

Furthermore, it would be desirable to provide fabrication techniques which would allow the aforementioned protection circuit to be integrated onto the ISFET's silicon substrate in a manner that avoids the difficulty in creating a metal electrode to serve as a reliable low-impedance contact with the liquid.

Further yet, it would be desirable to provide apparatus which utilize contact films that are resistant to chemical attack in many of the liquids that would be measured by the ISFET, without having to resort to the use of noble metals and intermediate layers to provide good adhesion for the film to the substrate.

SUMMARY OF THE INVENTION

Accordingly it is an object of the invention to provide methods and apparatus for measuring ions in a liquid and which inherently protect the apparatus from the effects of electrostatic discharge.

It is a further object of the invention to provide techniques for fabricating the aforementioned apparatus (i.e., apparatus for measuring ions in a liquid integrated with electrostatic discharge protection circuitry), on a silicon wafer.

More particularly, it is an object of the invention to provide electrostatic discharge protection to ISFET based devices used to selectively measure ions in a liquid.

Furthermore, it is an object of the invention to provide methods and apparatus which offer ESD protection to ISFET based devices used to selectively measure ions in a liquid, using (a) an ESD protection circuit made up of conventional protective elements integrated onto the same silicon chip on which the ISFET is formed; and (b) an interface means, in contact with the liquid being measured, which does not open up paths for D.C. leakage currents between the ISFET and the liquid.

Still further, it is an object of the invention to provide chip fabrication techniques which would allow the aforementioned protection circuit to be integrated onto the ISFET's silicon substrate in a manner that avoids the difficulty in creating a metal electrode to serve as a reliable low-impedance contact with the liquid.

Further yet, it is an object of the invention to provide ISFET based apparatus for measuring ions in a liquid that utilizes non-metallic contact films which are resistant to chemical attack, and which do not require the use of intermediate layers to provide good adhesion for the film to the substrate.

According to one aspect of the invention, an ESD protection circuit, made up of conventional protective elements, is integrated onto the same silicon chip on which the ISFET is formed, along with a novel interface. The novel interface is a structure, in contact with the liquid being measured, which does not open up paths for D.C. leakage currents between the ISFET and the liquid.

According to a preferred embodiment of the invention, a capacitor structure is used as the interface between the protection circuit and the liquid sample.

According to one specific aspect of the invention, apparatus for selectively measuring ions in a liquid, comprises: (a) a measuring circuit including a chemically sensitive ion sensor in the form of an ion sensitive field effect transistor (ISFET) formed on a silicon substrate; (b) an electrostatic discharge (ESD) protection circuit integrated onto the substrate; and (c) interface means, integrated onto the substrate, for providing an interface between the protection circuit and the liquid, characterized in that the interface means provides a contact with the liquid without opening up paths for D.C. leakage currents between the ISFET and the liquid.

According to a preferred embodiment of the invention, the interface means is a capacitor structure including (a) an electrode in electrical contact with the protection circuit; and (b) a capacitor dielectric in contact with the electrode and the liquid being measured.

Furthermore, according to a preferred embodiment of the invention, (a) the aforementioned electrode is a metal film exhibiting the characteristic that its oxide is an insulator (examples of suitable metal film include aluminum, antimony, hafnium, niobium, tantalum, tungsten, yttrium and zirconium); and the aforementioned capacitor dielectric is the oxide of the metal chosen for use as the electrode. The term "metal film" as used herinafter is defined to mean a metal film exhibiting the characteristic that its oxide is an insulator.

Still further, according to a preferred embodiment of the invention, the protection circuit includes means for transferring charge built up in a liquid test sample as a result of an ESD event. The means for transferring charge (to the source, drain and substrate of the ISFET included in the sensor), includes: (a) a first bi-directional zener diode between the aforementioned interface means and the source of the ISFET; (b) a second bi-directional zener diode between the interface means and the drain of the ISFET; and (c) a uni-directional zener diode between the interface means and the substrate.

Further aspects of the invention are directed to methods per se for providing ESD protection for ISFET sensors utilizing the interface means (e.g, capacitor structure) referred to hereinabove, and processes for fabricating the novel interface on a silicon wafer.

In particular, one further aspect of the invention is directed to a method for providing electrostatic discharge (ESD) protection to ion sensitive field effect transistor (ISFET) based ion selective electrodes, comprising the steps of: (a) forming an ISFET circuit on a silicon chip; (b) integrating a protection circuit onto the chip on which the ISFET is formed; and (c) integrating, onto the chip, an interface between the protection circuit and the liquid, wherein the interface provides a contact with the liquid without opening up paths for D.C. leakage currents between the ISFET and the liquid.

Fabrication processes contemplated by yet another aspect of the invention include a process for fabricating a capacitor to serve as an interface between a liquid being measured and a protection circuit included on an ion sensitive field effect transistor (ISFET) chip, wherein the ISFET chip is used to measure ions in the liquid and further wherein the chip includes a silicon substrate, a field oxide layer and at least one chemical barrier layer, and a diffused P+ region for connecting the capacitor to the protection circuit, comprising the steps of: (a) opening a via in the field oxide and the at least one chemical barrier layer; (b) sputter depositing a metal film onto the chip to create a lower electrode for the capacitor; (c) connecting the film to the diffused P+ region through the via; and (d) forming the oxide of said metal film to serve as the dielectric for the capacitor.

The invention features ISFET subassemblies, built in accordance with the teachings of the present invention, that when used in sensor probes have survived multiple exposure to ESD levels of 20,000 volts when tested in accordance with the IEC 801-2 standard.

Furthermore, the invention features chip fabrication techniques which would allow the aforementioned protection circuit to be integrated onto the ISFET's silicon substrate in a manner that avoids the difficulty in creating a metal electrode to serve as a reliable low-impedance contact with the liquid sample being tested. Still further, the use of a non-metallic contact film, as contemplated by the invention, resists chemical attack, and does not require the use of intermediate layers to provide good adhesion for the film to the substrate.

These and other objects, embodiments and features of the present invention and the manner of obtaining them will become apparent to those skilled in the art, and the invention itself will be best understood by reference to the following Detailed Description read in conjunction with the accompanying Drawing.

DETAILED DESCRIPTION

As indicated hereinabove, it is known that ESD damage can be prevented by using protection circuitry (within an ISFET based probe assembly) that allows build up of charge in a test sample during an ESD event, while simultaneously transferring the charge to the ISFET's source, drain and substrate. Such an approach minimizes the field developed across the transistor's insulator structure by rapidly equalizing charges on either side of the insulator during an ESD event.

Figure 1:
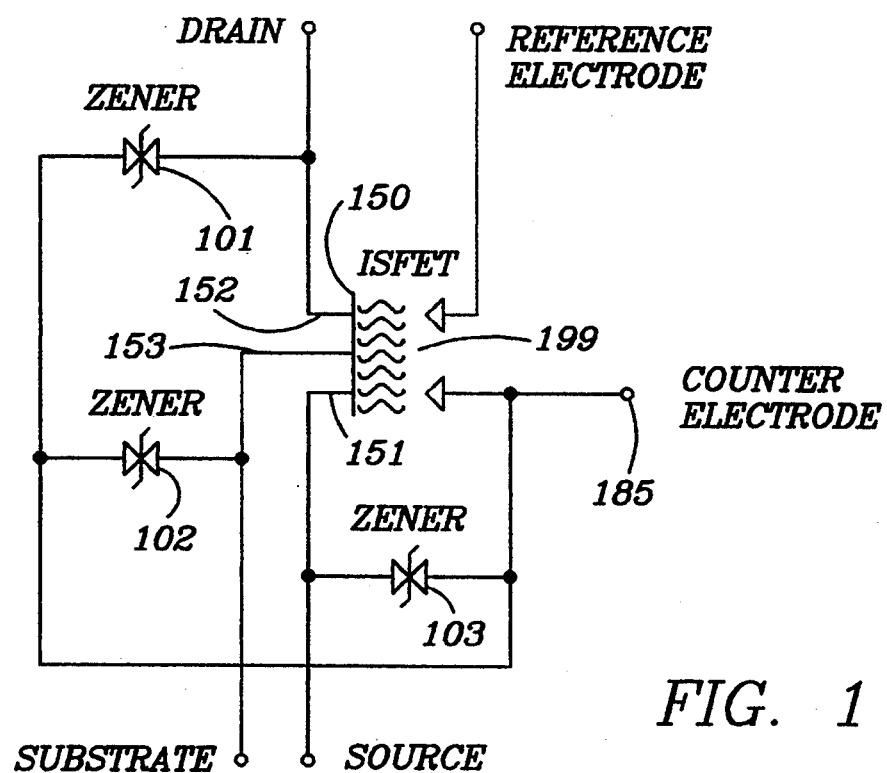
FIG. 1 depicts an illustrative protection circuit, within an ISFET based probe assembly, that allows build up of charge in a liquid test sample during an ESD event, while simultaneously transferring the charge to the ISFET's source, drain and substrate.

An exemplary protection circuit (within an ISFET based probe assembly), that allows build up of charge in a test sample during an ESD event, while simultaneously transferring the charge to the ISFET's source, drain and substrate, is illustrated in FIG. 1.

As shown in FIG. 1, the exemplary protection circuit (which is similar to the circuit described in the incorporated U.S. Pat. No. 4,589,970 patent), uses fast zener bi-directional diodes 101–103, connected to test liquid 199 and the source (151), drain (152) and substrate (153) conductors of ISFET 150. The electrical contact to test liquid 199 is achieved with the use of a counter electrode (185) which, as indicated hereinbefore, may be realized in accordance with teachings of U.S. Pat. No. 4,851,104, previously incorporated herein by reference.

The operation of the exemplary protection circuit depicted in FIG. 1 may be summarized as follows. In the event of an ESD occurrence, charge can be expected to build up in test sample 199 until the zener breakdown voltage is achieved.

Assuming a bi-directional zener voltage of a value substantially less than that needed to damage the device, once that voltage is exceeded, in either direction, the charge will be conducted between counter electrode 185 and the ISFET source, drain and substrate depicted in FIG. 1. Because differential insulator voltage is limited to the zener break down voltage, the insulator and ISFET sensor itself is protected.

Those skilled in the art will recognize that the interconnect distance between the liquid contact point through zener diodes 101–103, to the source, drain, and substrate conductors, is important. Because the duration of an ESD event is of the order of magnitude of 30 nanoseconds, at an approximate speed of light of 1 foot per nanosecond, the pathway between counter electrode 185 and silicon terminals must be limited to a distance of the order of magnitude of 2.4 inches, If this approximate distance is exceeded, insufficient time is available to transfer charge between the counter and silicon electrodes to limit insulator fields to 200 volts.

This distance requirement precludes the possibility of locating the zeners external to the electrode and strongly argues for function integration either on or in close proximity to the silicon chip.

As indicated hereinabove, U.S. Pat. No. 4,589,970, to Ligtenberg et al. (previously incorporated herein by reference), describes the use of the circuit similar to that shown in FIG. 1. The incorporated U.S. Pat. No. 4,589,970 patent also states that uni-direction zener diodes, capacitors, mechanical switches and high threshold voltage MOSFETS can be used in place of or in parallel with the bi-directional zeners.

Furthermore, as indicated hereinbefore, the use of discrete components mounted in the probe package to form the protection circuit and/or the integration of the circuit onto the ISFET's silicon substrate is also proposed by the incorporated U.S. Pat. No. 4,589,970 patent.

As pointed out in the Background of the Invention, a significant problem concerning the integration of the protection circuit described in the incorporated U.S. Pat. No. 4,589,970 patent (and any similar circuitry) onto the ISFET's silicon substrate, is the difficulty in creating a metal electrode that provides a reliable low-impedance contact to the liquid.

The incorporated U.S. Pat. No. 4,589,970 patent suggests the use of aluminum or polysilicon films to form the contact; however, as pointed out hereinbefore, both films are subject to chemical attack in many of the liquids that would be measured by the ISFET.

The alternative of depositing a film comprised of a noble metal for the contact and the associated requirement for an intermediate layer using materials such as titanium or chromium to provide good adhesion to the substrate, etc. (as described hereinbefore, along with other problems associated with using a noble metal contact), mitigate against the use of the noble metal alternative.

Instead, according to one aspect of the invention, an interface means (preferably a capacitor structure), is used to provide an interface between the test liquid and the protection circuitry made up of conventional circuit elements.

Figure 2:
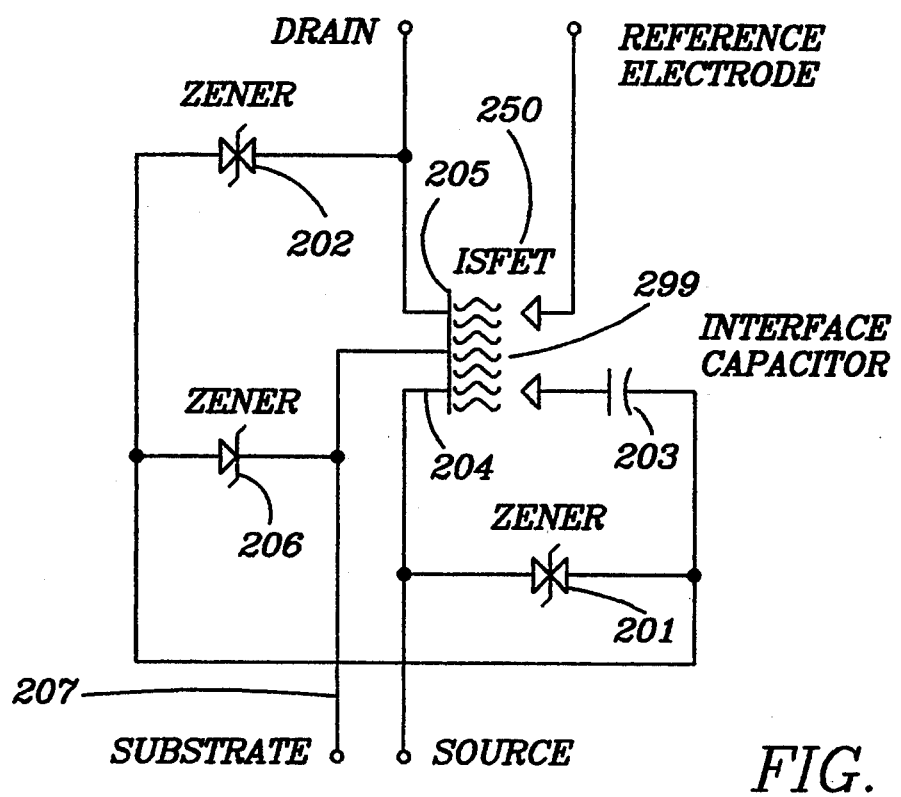
FIG. 2 depicts a protection circuit for an ISFET based sensor that includes interface means in the form of the capacitor structure of the type contemplated by a preferred embodiment of the invention.

Reference should be made to FIG. 2 which, as indicated hereinabove, depicts a protection circuit that includes interface means contemplated by the invention, combined with most of the same circuit elements described with reference to FIG. 1. These include bi-directional zener diodes 201 and 202 shown respectively between the interface means 203 (shown as the preferred interface capacitor, which is referred to hereinafter as interface capacitor 203), and source 204, and drain 205; as well as a uni-directional zener diode 206, shown between interface capacitor 203 and the substrate (207).

During an ESD event, charge will build up in the liquid being tested (shown as 299 in FIG. 2), as described above with reference to FIG. 1. Interface capacitor 203 couples the ESD pulse to zeners 201, 202 and 206. As the voltages across the zeners exceed their breakdown voltages the pulse is in turn coupled to the source, drain and substrate of ISFET 250. The field across the ISFET 250 gate region is minimized.

The primary advantage of the use of a capacitor to provide an interface between the liquid and the protection circuit is that no metal electrode is in contact with the liquid.

The problem of choosing a suitable contact metal or combination of metals is eliminated. Another advantage of the use of a capacitor is that D.C. leakage current paths that might exist between the liquid and the ISFET source, drain or substrate via the protection circuit are substantially curtailed.

Figure 3:
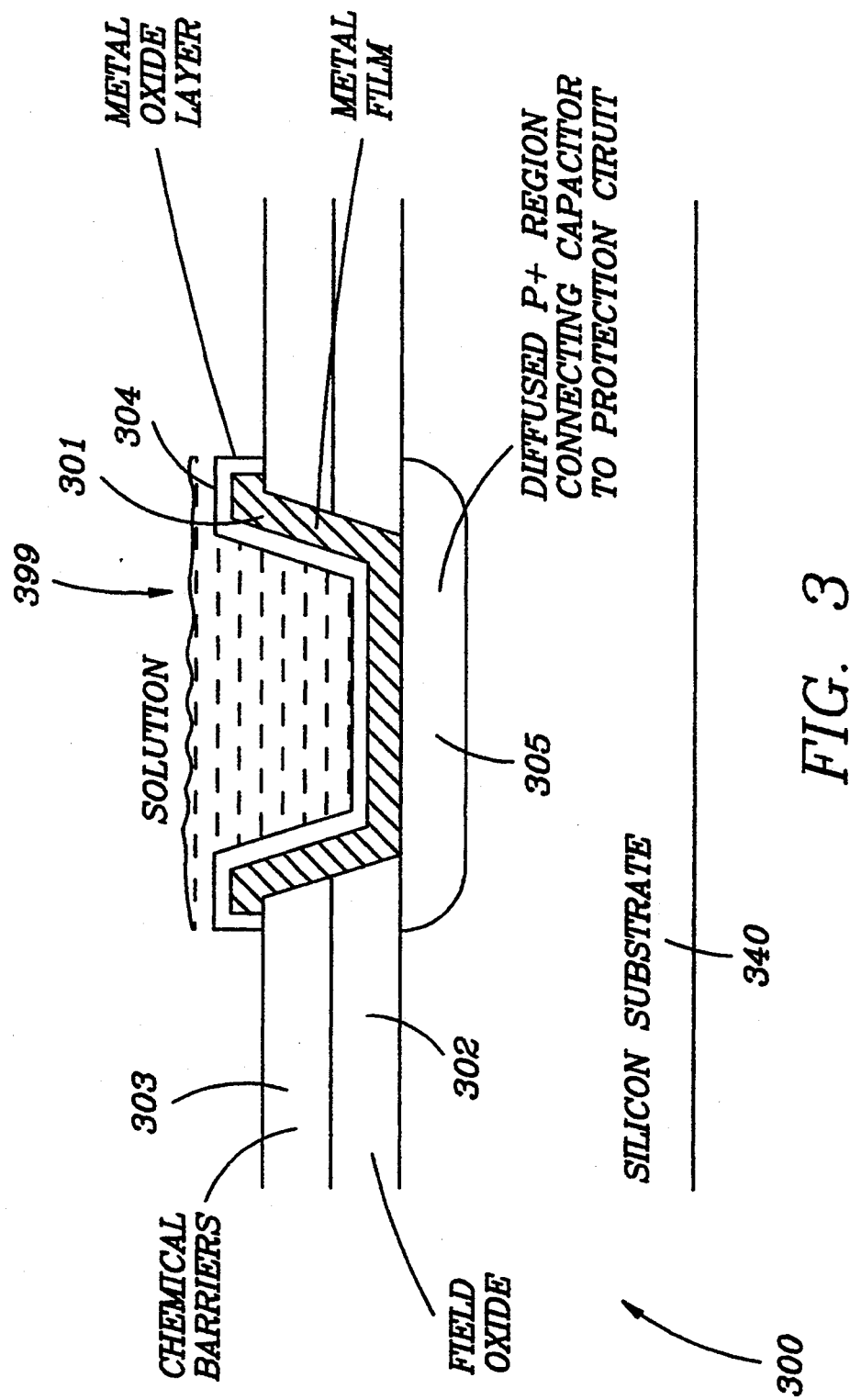
FIG. 3 depicts the structure of an exemplary interface capacitor, of the type contemplated by one aspect of the invention, as fabricated on a silicon wafer.

Reference should now be made to FIG. 3 which shows the structure of an exemplary interface capacitor (capacitor 300) which, in accordance with one aspect of the invention, is integrated on silicon substrate 340 with the other ESD protection elements shown in FIG. 2.

According to a preferred embodiment of the invention, the lower electrode of capacitor 300 (i.e., electrode 301), consists of a sputter deposited metal film. In FIG. 3, the metal film is shown connected to the other circuit elements on the chip through a via opened in the field oxide (layer 302) and other deposited films (layer(s) 303) used as chemical barriers. Through chemical or anodic oxidation of the metal film, an oxide film layer (304) may be formed to serve as the capacitor dielectric. According to the preferred embodiment of the invention, test liquid 399 is in contact with the capacitor dielectric.

Figure 4:
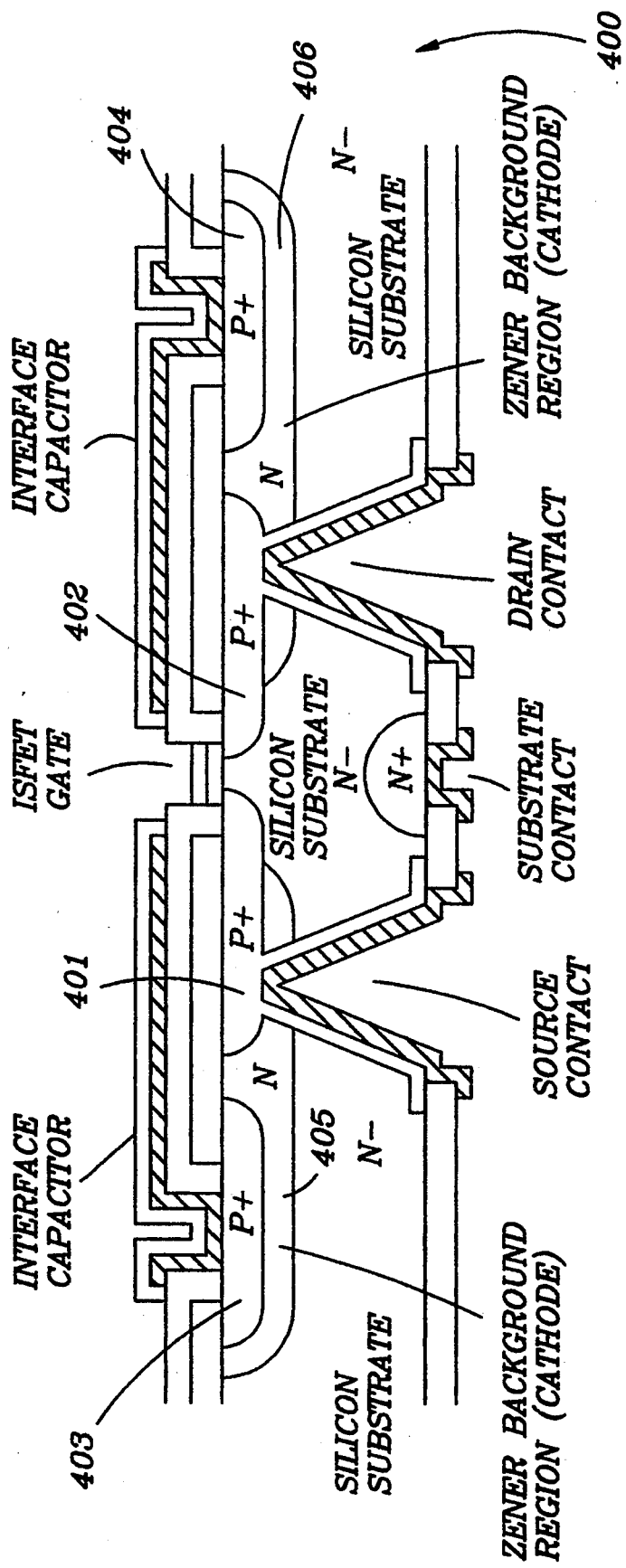
FIG. 4 depicts an example of how the ISFET, protection circuit and interface means combination contemplated by the invention may be implemented on silicon substrate.

Reference should now be made to FIG. 4 for an illustration of how the structure of the ISFET and the protection circuit contemplated by the invention can be implemented on silicon substrate 400.

FIG. 4 depicts two of the boron diffused P+ regions, 401 and 402, serving both as the source and drain respectively of the depicted ISFET. Regions 401 and 402 also serve as anodes for the protective zener diodes depicted in FIG. 2. The other two boron diffused P+ regions illustrated in FIG. 4 (regions 403 and 404), serve as anodes for both the bi-directional and uni-directional zeners which are depicted in FIG. 2.

The cathode or background for the zeners is provided by the phosphorus diffused N regions, 405 and 406. Selection of the dopant surface concentration and the junction depth for the N region determines the zener breakdown voltage. The terminals for the source, drain and substrate of the ISFET are provided on the backside of the substrate.

Those skilled in the art will now readily appreciate (with reference to FIGS. 2–4), that according to one specific aspect of the invention, apparatus for selectively measuring ions in a liquid, includes: (a) a measuring circuit including a chemically sensitive ion sensor in the form of an ion sensitive field effect transistor (ISFET) formed on a silicon substrate (where the ISFET may be on formed on the substrate as shown in FIG. 4); (b) an electrostatic discharge (ESD) protection circuit (of the type described with reference to FIG. 2,) integrated onto the substrate (also as shown by way of example in FIG. 4); and (c) interface means, integrated onto the substrate, for providing an interface between the protection circuit and the liquid, characterized in that the interface means provides a contact with the liquid without opening up paths for D.C. leakage currents between the ISFET and the liquid.

It may also be seen with reference to FIGS. 3–4 that, according to a preferred embodiment, the invention contemplates a process for fabricating: (a) a capacitor to serve as an interface between a liquid (such as liquid 399 shown in FIG. 3) being measured; and (b) a protection circuit included on an ion sensitive field effect transistor (ISFET) chip (such as the chip shown in FIG. 4), wherein the ISFET chip is used to measure ions in the liquid and further wherein the chip includes a silicon substrate (shown, for example as substrate 340 in FIG. 3), a field oxide layer (302 in FIG.3) and at least one chemical barrier layer (303 in FIG. 3), and a diffused P+ region (305 in FIG. 3) for connecting the capacitor to the protection circuit, comprising the steps of: (a) opening a via in the field oxide and the at least one chemical barrier layer; (b) sputter depositing a metal film onto the chip to create a lower electrode for the capacitor; (c) connecting the film to the diffused P+ region through the via; and (d) forming the oxide of the metal film to serve as the dielectric for the capacitor. All of the aforementioned steps have been previously described herein with reference to FIG. 3.

What has been described in detail hereinabove are methods, apparatus and chip fabrication techniques which meet all of the aforestated objectives. As previously indicated, those skilled in the art will recognize that the foregoing description has been presented for the sake of illustration and description only. It is not intended to be exhaustive or to limit the invention to the precise form disclosed, and obviously many modifications and variations are possible in light of the above teaching.

The embodiments and examples set forth herein were presented in order to best explain the principles of the instant invention and its practical application to thereby enable others skilled in the art to best utilize the instant invention in various embodiments and with various modifications as are suited to the particular use contemplated.

In view of the above it is, therefore, to be understood that the claims appended hereto are intended to cover all such modifications and variations which fall within the true scope and spirit of the invention.

What is claimed is:

1. Apparatus for selectively measuring ions in a liquid, comprising:
   (a) a measuring circuit including a chemically sensitive ion sensor in the form of an ion sensitive field effect transistor (ISFET) formed on a silicon substrate;
   (b) an electrostatic discharge (ESD) protection circuit integrated onto said substrate; and
   (c) interface means, integrated onto said substrate, for providing an interface between said protection circuit and said liquid, characterized in that said interface means provides a contact with said liquid without opening up paths for D.C. leakage currents between the ISFET and said liquid.

2. Apparatus as set forth in claim 1 wherein said interface means further comprises a capacitor structure.

3. Apparatus as set forth in claim 2 wherein said capacitor structure further comprises:
   (a) an electrode in electrical contact with said protection circuit; and
   (b) a capacitor dielectric in contact with said electrode and the liquid being measured.

4. Apparatus as set forth in claim 3 wherein said electrode is a metal film.

5. Apparatus as set forth on claim 3 wherein said capacitor dielectric is an oxide of said metal film.

6. Apparatus as set forth in claim 1 wherein said protection circuit further comprises:
   (a) a first bi-directional zener diode between said interface means and the source of said ISFET;
   (b) a second bi-directional zener diode between said interface means and the drain of said ISFET; and
   (c) a uni-directional zener diode between said interface means and said substrate.

7. Apparatus as set forth in claim 6 wherein said interface means further comprises a capacitor structure.

8. Apparatus for providing electrostatic discharge (ESD) protection to an ion sensitive field effect transistor (ISFET) based measuring device used to measure ion activity in a liquid, comprising:
   (a) an ESD protection circuit fabricated on a silicon substrate, including:
      (a1) a first bi-directional zener diode coupled to the source of said ISFET;
      (a2) a second bi-directional zener diode coupled to the drain of said ISFET; and
      (a3) a uni-directional zener diode coupled to said substrate; and
   (b) interface means, integrated onto said substrate together with said ESD protection circuit, for providing an interface between said protection circuit and said liquid without opening up paths for D.C. leakage currents between the ISFET and said liquid.

9. Apparatus as set forth in claim 8 wherein said interface means is connected in series with each of said first bi-directional zener diode, said second bi-directional zener diode, and said uni-directional zener diode.

10. Apparatus for providing electrostatic discharge (ESD) protection to an ion sensitive field effect transistor (ISFET) based sensor chip used to measure ion activity in a liquid test sample, comprising:
    (a) means for transferring charge, built up in said liquid test sample as a result of an ESD event, to the source, drain and substrate of said ISFET; and
    (b) interface means, integrated onto said chip together with said means for transferring charge, for providing an interface between said protection circuit and said liquid without opening up paths for D.C. leakage currents between the ISFET and said liquid.

11. Apparatus as set forth on claim 10 wherein said interface means further comprises a capacitor structure.

12. Apparatus for providing electrostatic discharge (ESD) protection to an ion sensitive field effect transistor (ISFET) based sensor chip used to measure ion activity in a liquid test sample, comprising:
    (a) means for building up charge in said test sample during an ESD event; and
    (b) means for transferring charge built up in said liquid test sample, as a result of said ESD event, to the source, drain and substrate of said ISFET.

13. Apparatus as set forth in claim 12 wherein said means for building up charge and said means for transferring charge are integrated onto said chip.

* * * * *